(12) United States Patent
Corum et al.

(10) Patent No.: US 6,922,235 B2
(45) Date of Patent: Jul. 26, 2005

(54) DETECTING A DEFECT OF AN INTEGRATED CIRCUIT

(75) Inventors: Daniel Lee Corum, Richardson, TX (US); Taylor Jon Lowry, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 253 days.

(21) Appl. No.: 10/140,407

(22) Filed: May 6, 2002

(65) Prior Publication Data

US 2003/0206293 A1 Nov. 6, 2003

(51) Int. Cl.[7] .............................................. G01N 21/88
(52) U.S. Cl. ................................... 356/237.1; 356/446
(58) Field of Search ........................... 356/237.1, 237.4, 356/237.5, 445–448

(56) References Cited

U.S. PATENT DOCUMENTS 5,903,343 A * 5/1999 Ning et al. .............. 356/241.1

* cited by examiner

Primary Examiner—Richard A. Rosenberger
(74) Attorney, Agent, or Firm—Jacqueline J. Garner; W. James Brady, III; Frederick J. Telecky, Jr.

(57) ABSTRACT

Detecting a defect of an integrated circuit includes illuminating an integrated circuit with an optical beam. The integrated circuit includes a substrate, a dielectric layer disposed outwardly from the substrate, and a sequence of metal links disposed within the dielectric layer. An end metal link of the sequence of metal links is grounded. A change of relative brightness of the dielectric layer proximate to the sequence of metal links is detected. The change of relative brightness comprises a difference between a first brightness associated with a first metal link and a second brightness associated with a second metal link coupled to the first metal link. The change of relative brightness is associated with a defect of the integrated circuit.

9 Claims, 3 Drawing Sheets

DETECTING A DEFECT OF AN INTEGRATED CIRCUIT

TECHNICAL FIELD OF THE INVENTION

This invention relates generally to the field of semiconductor devices and more specifically to detecting a defect of an integrated circuit.

BACKGROUND OF THE INVENTION

Electronic equipment such as televisions, telephones, radios, and computers typically include semiconductor components such as integrated circuits. In an effort to improve integrated circuits, different techniques for producing integrated circuits are tested. To test a technique, integrated circuits produced using the technique are examined for defects. The defects are studied to determine how to improve the technique. Known methods of detecting defects in an integrated circuit, however, often cannot detect certain types of defects. Consequently, known methods for detecting defects are not satisfactory in many situations.

SUMMARY OF THE INVENTION

In accordance with the present invention, disadvantages and problems associated with techniques for detecting a defect of an integrated circuit may be reduced or eliminated.

According to one embodiment of the present invention, detecting a defect of an integrated circuit includes illuminating an integrated circuit with an optical beam. The integrated circuit includes a substrate, a dielectric layer disposed outwardly from the substrate, and a sequence of metal links disposed within the dielectric layer. An end metal link of the sequence of metal links is grounded. A change of relative brightness of the dielectric layer proximate to the sequence of metal links is detected. The change of relative brightness comprises a difference between a first brightness associated with a first metal link and a second brightness associated with a second metal link coupled to the first metal link. The change of relative brightness is associated with a defect of the integrated circuit.

Certain embodiments of the invention may provide technical advantages. A technical advantage of one embodiment may include detecting defects of integrated circuits that are not detectable using known passive voltage contrast techniques. According to passive voltage contrast techniques, a scanning electron microscope is used to detect defects. Some defects, however, do not create a sufficiently large voltage difference to be detected by the scanning electron microscope. Another technical advantage of one embodiment may include detecting defects in integrated circuits having protective overcoats. Known passive voltage contrast techniques, however, may have difficulty detecting defects in integrated circuits having protective overcoats. Another technical advantage of one embodiment may be that an optical microscope may be used to detect defects instead of using a scanning electron microscope. Scanning electron microscopes are typically harder to obtain and require more preparation of samples to be tested.

Examples of the invention may include none, some, or all of these technical advantages. One or more other technical advantages may be readily apparent to one skilled in the art from the figures, descriptions, and claims included herein.

BRIEF DESCRIPTION OF THE DRAWINGS

For a more complete understanding of the present invention and for further features and advantages, reference is now made to the following description, taken in conjunction with the accompanying drawings, in which.

DETAILED DESCRIPTION OF THE DRAWINGS

Embodiments of the present invention and its advantages are best understood by referring to FIGS. 1 through 5 of the drawings, like numerals being used for like and corresponding parts of the various drawings.

Figure 1:
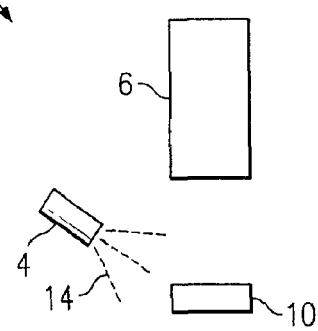
FIG. 1 illustrates an example system for detecting a defect of an integrated circuit.

FIG. 1 illustrates an example system 2 for detecting a defect of an integrated circuit 10. Integrated circuit 10 may comprise, for example, an integrated circuit produced according to a manufacturing technique that is being tested. System 2 is used to examine integrated circuit 10 to detect a change of resistance that may indicate a defect of integrated circuit 10. According to one embodiment, a source 4 produces an optical beam 14 that illuminates integrated circuit 10 to reveal a defect of integrated circuit 10. Optical beam 14 may have any suitable wavelength range, for example, a wavelength range within the visible spectrum. An optical microscope 6 may be used to view integrated circuit 10, and specifically to view reflected light caused by optical beam 14. Optical microscope 6 may provide any suitable magnification, for example, between five times to two thousand times.

Figure 2:
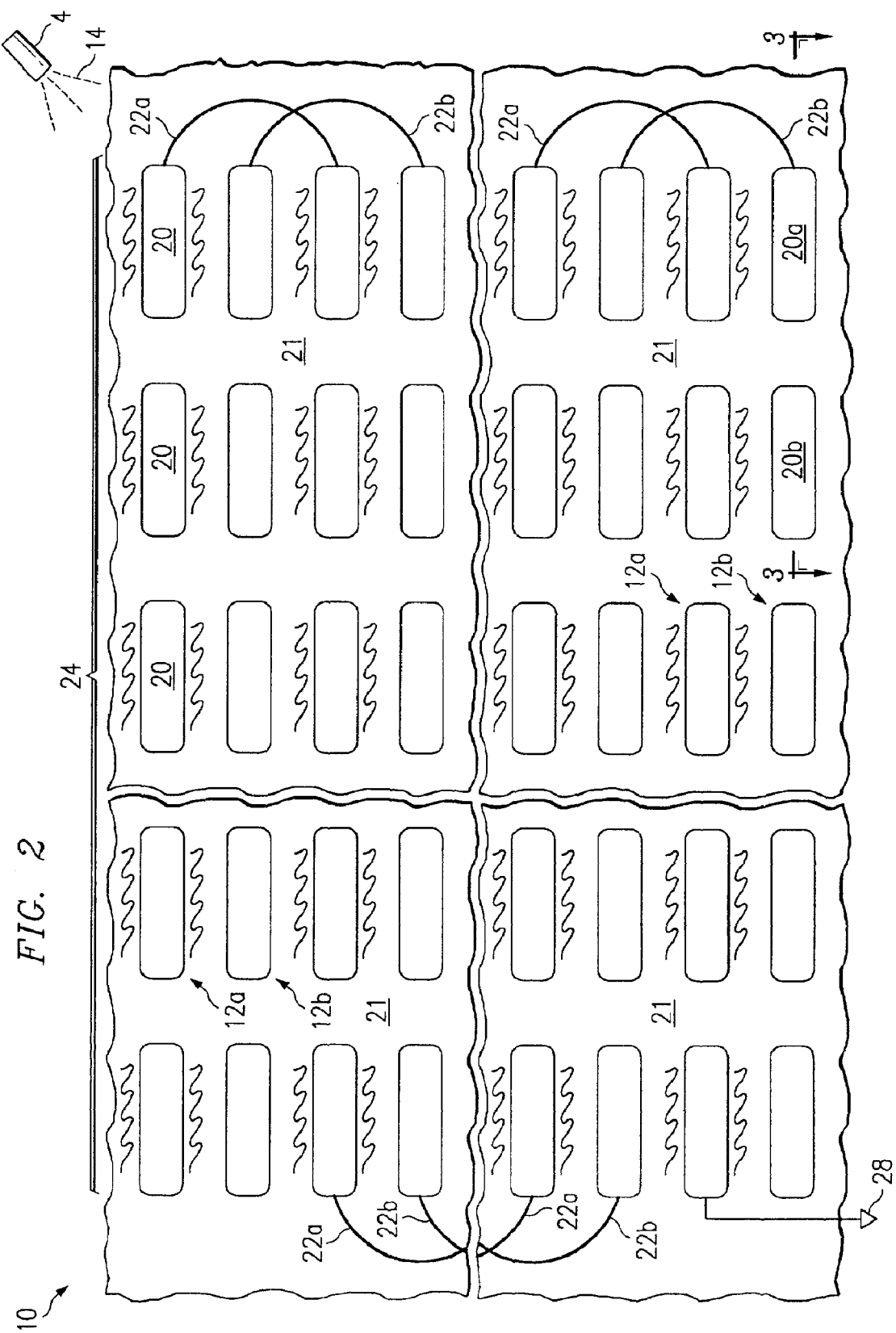
FIG. 2 illustrates an example integrated circuit with via chains.

FIG. 2 illustrates a top view of integrated circuit 10 having via chains 12. A via chain 12 comprises metal links 20 and connectors 22. Via chain 12 may be a test structure. Metal links 20 may comprise, for example, copper, aluminum, or other suitable conductive material. Metal links 20 may be formed in a dielectric layer 21, which is described in more detail with reference to FIG. 3. Metal links 20 of via 12 are coupled together, as described in more detail with reference to FIG. 3. A number of metal links 20 may be coupled together to form a line 24 of via chain 12. A connector 22 may couple lines 24 of via chain 12. Metal links 20 of via chain 12 form a sequence of metal links that may conduct a current. Via chain 12a may be coupled to a ground 28, and via chain 12b may be floating.

In the illustrated example, via chain 12a is grounded, and via chain 12b is not grounded. Under illumination by optical beam 14, dielectric layer 21 proximate to via chain 12a may appear to be darker than dielectric layer 21 proximate to via chain 12b. The darkening may result from, for example, photons from optical beam 14 creating a photocell effect in dielectric layer 21 proximate to grounded via chain 12a. The photocell effect may cause dielectric layer 21 to reflect light such that it appears darker. The darkening, however, may result from other effects in addition to or instead of such photocell effect.

Figure 3:
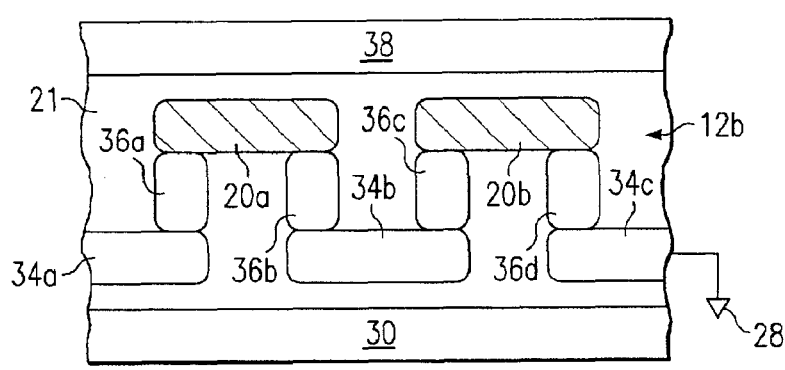
FIG. 3 illustrates a cutaway view of the integrated circuit of FIG. 2.

FIG. 3 illustrates a cutaway view of via chain 12b of integrated circuit 10 of FIG. 2. Integrated circuit 10 includes a substrate 30, dielectric layer 21, via chain 12b and a protective overcoat 38. Substrate 30 may comprise any suitable semiconductive material such as silicon having any suitable thickness. Dielectric layer 21 may comprise any suitable dielectric formed using a suitable growth or deposition technique to a suitable thickness. According to one embodiment, dielectric layer 21 comprises a high resistance, low dielectric constant K dielectric material such as organo-silicate glass (OSG). Dielectric constant K may range from approximately 2.5 to 3.5, for example, 2.9. Other suitable dielectric material, however, may be used for dielectric layer 21.

Via chain 12b comprises metal links 34, vias 36, and metal links 20. Metal links 34 and 20 are formed on different levels of integrated circuit 10. Metal links 34 and 20 on different levels may be interconnected using vias 36 that provide electrical connections from metal links 34 of one layer to metal links 20 of another layer. Metal links 34 are disposed outwardly from substrate 30, and may comprise, for example, any suitable conductive material such as copper or aluminum having a thickness of approximately 250 to 350 nanometers.

Vias 36 are formed outwardly from metal links 34. During formation of vias 36, via openings of a suitable aspect ratio are etched in dielectric layer 21. A via fill is deposited in the via opening to form via 36. The via fill may comprise, for example, any suitable conductive material such as copper or aluminum. Metal links 20 are formed outwardly from vias 36. Metal links 20 may comprise, for example, any suitable conductive material such as copper or aluminum having a thickness of approximately 250 to 350 nanometers. Vias 36 couple metal links 34 and 20 in order to form a sequence of coupled metal links 34 and 20 of via chain 12b. Protective overcoat 38 may be disposed outwardly from dielectric layer 21. Protective overcoat 38 may comprise, for example, a chemical vapor deposition (CVD) oxide such as fluorinated silicate glass (FSG) deposited to a thickness of approximately 600 nanometers.

Figure 4:
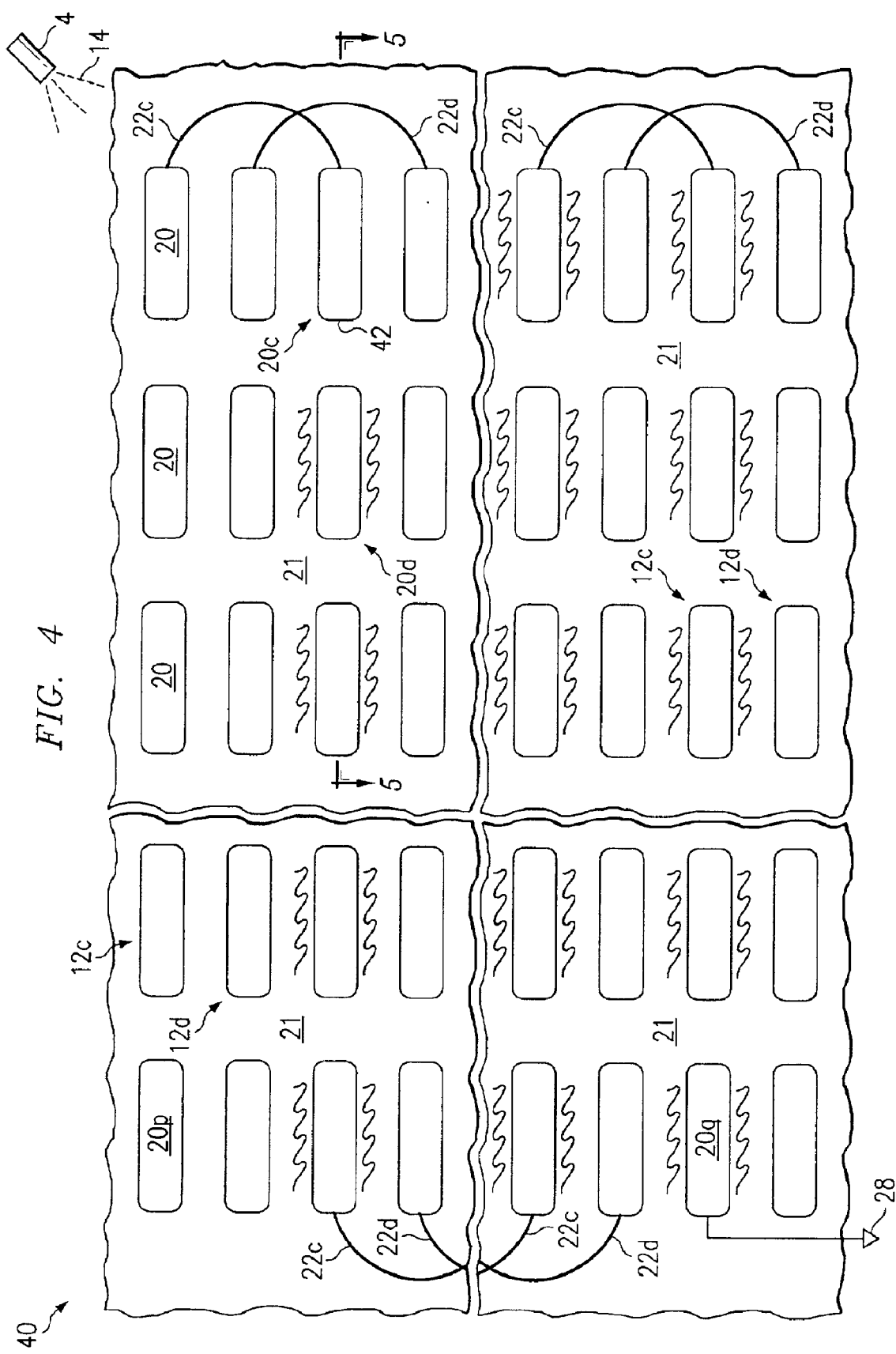
FIG. 4 illustrates an example integrated circuit having a defect.

FIG. 4 illustrates an example integrated circuit 40 having a defect 42. Integrated circuit 40 may be substantially similar to integrated circuit 10, except integrated circuit 40 has defect 42. Optical beam 14 illuminates integrated circuit 40. Dielectric layer 21 proximate to floating via chain 12d appears to be bright. Dielectric layer 21 appears bright proximate to the portion of via chain 12c from end metal link 20p to metal link 20c, and dark proximate to the portion of via chain 12c from metal link 20d to end metal link 20q coupled to ground 28. A change in brightness of between dielectric layer 21 proximate to metal link 20c and dielectric layer 21 proximate to metal link 20d indicates a region of higher resistance, which may comprise defect 42. As previously discussed, this darkening may be due to photons creating a photocell effect in dielectric layer 21 proximate to the portion of via chain 12c coupled to ground 28.

Figure 5:
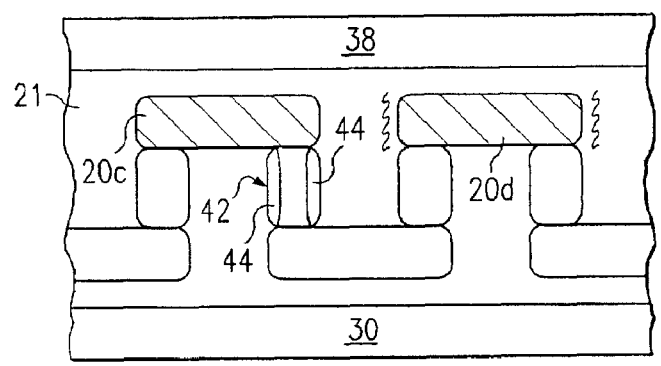
FIG. 5 illustrates a cutaway view of the integrated circuit of FIG. 4.

FIG. 5 illustrates a cutaway view of integrated circuit 40 of FIG. 4. Dielectric layer 21 proximate to metal link 20d appears to be darker than dielectric layer 21 proximate to metal link 20c, indicating an area of higher resistance comprising defect 42. In the illustrated example, defect 42 comprises regions 44 in which the via fill was not deposited. Regions 44 may comprise, for example, insulative material, contamination, voids, or other non-fill material. Defect 42, however, may comprise any type of formation that results in higher resistance between metal link 20c and metal link 20d. Defect 42 may be caused by, for example, residual deposit, particulate matter, or impurities. For example, defect 42 may result from stringers formed from residual material within a via opening or from incomplete removal of photoresist used to form the via opening, both of which may block deposition of via fill into the via opening. Although the illustrated example uses a structure comprising links and vias, the structure may comprise any suitable metal traces, with or without links or vias.

Certain embodiments of the invention may provide technical advantages. A technical advantage of one embodiment may include detecting defects of integrated circuits 10 that are not detectable using known passive voltage contrast techniques. According to passive voltage contrast techniques, a scanning electron microscope is used to detect defects. Some defects, however, do not create a sufficiently large voltage difference to be detected by the scanning electron microscope. Another technical advantage of one embodiment may include detecting defects in integrated circuits 10 having protective overcoats 38. Known passive voltage contrast techniques, however, may have difficulty detecting defects in integrated circuits 10 having protective overcoats 38. Another technical advantage of one embodiment may be an optical microscope 6 may be used to detect defects instead of using a scanning electron microscope. Scanning electron microscopes are typically harder to obtain and require more preparation of the sample to be tested.

Although an embodiment of the invention and its advantages are described in detail, a person skilled in the art could make various alterations, additions, and omissions without departing from the spirit and scope of the present invention as defined by the appended claims.

What is claimed is:

1. A method for detecting a defect of an integrated circuit, comprising:

illuminating an integrated circuit with an optical beam, the integrated circuit comprising a substrate, a dielectric layer disposed outwardly from the substrate, and a sequence of metal links disposed within the dielectric layer, an end metal link of the sequence of metal links being grounded;

detecting a change of relative brightness of the dielectric layer proximate to the sequence of metal links, the change of relative brightness comprising a difference between a first brightness associated with a first metal link and a second brightness associated with a second metal link coupled to the first metal link; and associating the change of relative brightness with a defect of the integrated circuit.

2. The method of claim 1, wherein:

a first number of metal links between the first metal link and the end metal link is greater than a second number of links between the second metal link and the end metal link; and the first brightness associated with the first metal link is greater than the second brightness associated with the second metal link.

3. The method of claim 1, wherein associating the change in brightness with a defect of the integrated circuit comprises:

associating the change of relative brightness with a change of resistance; and associating the change of resistance with the defect of the integrated circuit.

4. The method of claim 1, wherein the sequence of metal links comprises a via chain comprising a plurality of vias coupling the metal links.

5. The method of claim 1, wherein the dielectric layer has a dielectric constant less within the range of approximately 2.5 to 3.5.

6. The method of claim 1, wherein the dielectric layer has a dielectric constant of approximately 2.9.

7. The method of claim 1, wherein the dielectric layer comprises an organo-silicate glass.

8. The method of claim 1, wherein the integrated circuit comprises a protective overcoat disposed outwardly from the dielectric layer.

9. A method for detecting a defect of an integrated circuit, comprising:

illuminating an integrated circuit with an optical beam, the integrated circuit comprising a substrate, a dielectric layer a sequence of metal links, and a protective overcoat, the dielectric layer disposed outwardly from the substrate and comprising an organo-silicate glass having a dielectric constant of approximately 2.9, the sequence of metal links disposed within the dielectric layer, the sequence of metal finks comprising a via chain comprising a plurality of vias coupling the metal links, an end metal link of the sequence of metal links being grounded, the protective overcoat disposed outwardly from the dielectric layer;

detecting a change of relative brightness of the dielectric layer proximate to the sequence of metal links, the change of relative brightness comprising a difference between a first brightness associated with a first metal rink and a second brightness associated with a second metal link coupled to the first metal link, a fist number of metal links between the first metal link and the end metal link being greater than a second number of links between the second metal link and the end metal link, and the first brightness associated with the first metal link being greater than the second brightness associated with the second metal link;

associating the change of relative brightness with a change in resistance; and associating the change in resistance with a defect of the integrated circuit.

* * * * *